US009816964B1

(12) United States Patent
Nguyen-Dinh et al.

(10) Patent No.: US 9,816,964 B1
(45) Date of Patent: Nov. 14, 2017

(54) ULTRASONIC METHOD AND DEVICE FOR VOLUMETRIC EXAMINATION OF ALUMINOTHERMIC RAIL WELDS (71) Applicants: Vermon S.A., Tours (FR); Christopher Michael Spree, Sittingbourne, Kent (GB); Simon-Peter Santospirito, Harrow, Middlesex (GB); Aasim Khalid, Harrow, Middlesex (GB)

(72) Inventors: An Nguyen-Dinh, La Riche (FR); Stephane Michau, La Riche (FR); Christopher Spree, Sittingbourne (GB); Simon-Peter Santospirito, London (GB); Aasim Khalid, Northwood (GB)

(73) Assignee: Vermon S.A., Tours (FR)

( * ) Notice: Subject to any disclaimer, the term of this patent is extended or adjusted under 35 U.S.C. 154(b) by 112 days.

(21) Appl. No.: 14/579,350

(22) Filed: Dec. 22, 2014

Related U.S. Application Data (63) Continuation of application No. 13/405,869, filed on Feb. 27, 2012, now abandoned.
(Continued)

(51) Int. Cl.
G01N 29/34 (2006.01)
G01N 29/06 (2006.01)
G01S 7/52 (2006.01)

(52) U.S. Cl.
CPC ........ G01N 29/069 (2013.01); G01N 29/34 (2013.01); G01S 7/52017 (2013.01);
(Continued)

(58) Field of Classification Search
CPC ......... G01N 29/265; G01N 2291/2623; G01N 29/041
(Continued)

(56) References Cited

U.S. PATENT DOCUMENTS 4,487,071 A * 12/1984 Pagano .................. G01N 29/07
73/612
7,770,847 B1 * 8/2010 Severson ............... A63H 19/24
246/1 C
(Continued)

OTHER PUBLICATIONS

Standard, NF EN 14730-2:2006, Dec. 2006 (French version of BS EN 14730-1:2006). English-language translation of the reference is not within the possession, custody, or control of, or readily available.

Primary Examiner — Amie M N'Dure
(74) Attorney, Agent, or Firm — Stites & Harbison, PLLC; Jeffrey A. Haeberlin (57) ABSTRACT An ultrasonic non-destructive testing method and device for rail applications uses a plurality of phased array transducers to inspect aluminothermit weld defects located in a head portion, a web portion, an ankle portion, and a toe portion of a weld of a rail section. The method includes: scanning the head portion of the weld including: a first phased array transducer positioned above the weld and a second phased array transducer positioned a distance from the first phased array transducer to provide inclined access to the weld; and scanning the toe portion of the weld including: positioning pairs of third, fourth, and fifth phased array transducers on a surface of the toe portion, such that the pairs of third, fourth and fifth phased array transducers are disposed symmetrically with one of the pair on each side of the toe portion.

6 Claims, 12 Drawing Sheets

Related U.S. Application Data

(60) Provisional application No. 61/446,790, filed on Feb. 25, 2011.

(52) U.S. Cl.
CPC ............... *G01N 2291/0234* (2013.01); *G01N 2291/0289* (2013.01); *G01N 2291/2623* (2013.01)

(58) Field of Classification Search
USPC ...................................... 73/618–620; 702/39
See application file for complete search history.

(56) References Cited

U.S. PATENT DOCUMENTS

| | | | | |
|---|---|---|---|---|
| 7,938,008 | B2 * | 5/2011 | Owens | G01N 29/043 73/599 |
| 8,070,108 | B2 * | 12/2011 | Severson | A63H 19/24 246/1 C |
| 8,196,469 | B2 * | 6/2012 | Pielli | G01N 29/262 702/104 |
| 2005/0279240 | A1 * | 12/2005 | Pedanekar | B61K 9/08 104/26.1 |
| 2010/0330875 | A1 * | 12/2010 | Severson | A63H 19/24 446/454 |
| 2012/0016542 | A1 * | 1/2012 | Severson | A63H 19/24 701/19 |
| 2014/0299715 | A1 * | 10/2014 | Severson | A63H 19/24 246/187 A |

\* cited by examiner

ULTRASONIC METHOD AND DEVICE FOR VOLUMETRIC EXAMINATION OF ALUMINOTHERMIC RAIL WELDS

CROSS-REFERENCE TO RELATED APPLICATIONS

This application is a continuation of prior application Ser. No. 13/405,869, filed Feb. 27, 2012, which claimed the benefit of U.S. Provisional Application No. 61/446,790, filed Feb. 25, 2011. Said prior applications are hereby incorporated by reference.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

This invention relates to an ultrasonic method and device for the examination and detection of defects of aluminothermic rail welds. More specifically, the invention relates to the use of a set of phased array transducers disposed on different surface portions of a rail associated with phased array beamforming electronic and transducer positioning systems to assist with transducer manipulation.

2. Description of the Related Art

In a "continuous welded rail" (CWR) technique commonly practiced in Europe to improve the quality of ride for passenger trains, rail joints are welded in-situ welding of using thermit welding. In this process, a highly exothermic reaction between aluminium and iron oxides results in the production of molten steel which is poured into a mould surrounding a gap to be welded. The thermit welding process includes the following steps: preparation of the rail cross section, placing the mould, preheating the rail portions to be welded, and ignition of the thermit reaction.

The procedure of "controlled localized reaction" to keep the thermit mixture ignition under control was invented by Dr Goldschmidt and, hence, the process is sometimes also known as the Goldschmidt process. Individually patented processes have led to different trade names such as "Thermit," "Boutte," "Argothem," etc.

Although aluminothermic welding is well proven for rails, it is none-the-less a critical safety component of the rail infrastructure. Yet these welds are not volumetrically inspected. According to European and British standards for railway applications BS EN 14730-1:2006, singles element ultrasonic transducers are used to inspect the rail welds at three different areas including head, web and ankle zones, each transducer is used to manually scan the corresponding surfaces with wedges shaped between 45 and 70 deg, this method is a highly time consuming operation and very operator dependent. Furthermore, single element transducers cannot be dynamically focused on defects when the transducer is moved, so the detection pertinence of the method is affected.

U.S. Pat. No. 3,960,005 to Vezina (hereinafter "Vez005"), discloses an ultrasonic testing device for thermit rail welds, including a longitudinal transducer shoe placed along the top surface of the rail and a plurality of single transducers to provide scanning of the rail depth. Vez005 also discloses an inclination of the transmit pulse of at least 45 degrees to address the depth of weld. Vez005 discloses detecting ultrasonic energy transmitted from different emitting transducers to indicate the ultrasonic transparency of the weld. This cannot be applied to the rail shoe inspection and, moreover, the method of Vez005 will work only on substantial size defects. No ultrasonic beam focusing is disclosed.

US Patent Application Publication No. US 2010/0307250 to Brignac et al. (hereinafter "Bri250") discloses a weld inspection device for inspecting internal defects of rail. The device comprises attachment structures assembled together by rods which play a role of linear guidance for a runner that carries ultrasonic probes and can be moved longitudinally with a top surface of a rail. The inspection device described by Bri250 employs several transmitter/detectors modules to transmit and receive at different angles to provide a full set of data from the region of interest by moving the runner alongside the rail. Although not mentioned, for one skilled in the art the angled transducers as described by Bri250 are assumed to be wedged to provide such a feature. No indication of electronic focusing nor electronic beam steering is found. With respect to the Bri250 description, a rail's aluminothermit weld can be inspected from the head to the ankle with a best detection performance expected for flaws located in the web of the rail because the transducer lateral resolution will favour flaws located within a certain distance from the surface of transducer. Such a device will exhibit poor sensitivity and resolution in some areas of the weld (near the top surface and at the ankle), furthermore, the toes of rail cannot be inspected according to this disclosure.

BRIEF SUMMARY OF THE INVENTION

It is desirable to provide an ultrasound methodology of non-destructive examination of the aluminothermic welds in volumetric manner to enhance defect detection rates and accuracy as well as the reliability of the inspection process.

It is also desirable to have an inspection device dedicated to rail's aluminothermit welds inspection that provides more comprehensive data from the weld at every region of weld, as well as providing higher flaw detection accuracy (sizing and localizing).

According to the disclosure of this invention, an ultrasonic method for examination of aluminothermic rail welds using a set of phased array transducers is concerned, a plurality of phased array transducers are positioned on several areas of the rail to provide inspection of defects/flaws in different regions of the weld section, the phased array transducers or probes are carried by a mechanical clamping structure which allows perfect positioning of the transducers on the rail when in action, the transducers are driven by a multi-channel beam forming electronics associated with a control and detection software to image and optionally to provide tools for acceptance of flaw level with automatic flaw threshold detection.

According to a first aspect of the invention, an ultrasonic non-destructive testing method for rail applications using a plurality of phased array transducers to inspect aluminothermit weld defects located in a head portion, a web portion, an ankle portion, and a toe portion of a weld of a rail section, includes the following steps:

scanning the head portion of the weld including: positioning a first phased array transducer and a second phased array transducer on the head portion of the rail section in longitudinal or head-to-tail configuration for the inspection of the head portion and the web portion of the weld, wherein the first phased array transducer is positioned above the weld and the second phased array transducer is positioned a distance from the first phased array transducer to provide inclined access to the weld; and     scanning the toe portion of the weld including: positioning a pair of third phased array transducers, a pair of fourth phased array transducers, and a pair of fifth phased array transducers on a surface of the toe portion, such that the pair of third phased array transducers are disposed symmetrically with one of the pair on each side of the toe portion, the pair of fourth phased array transducers are disposed symmetrically with one of the pair on each side of the toe portion, and the pair of fifth phased array transducers are disposed symmetrically with one of the pair on each side of the toe portion.

This aspect regards a ultrasonic non-destructive testing method for a rail weld wherein is described a methodology for positioning and orienting of phased array transducers on rail section surfaces to provide accurate scanning of critical regions such as the head portion, the web portion, the ankle portion, and the toe portion of the weld. This method also relates to transducer geometry and their locations on the rail section to reduce the duration of inspection as well as to improve detection accuracy.

According to a second aspect of the invention, a weld inspection ultrasonic device for non-destructive testing of an aluminothermit weld of a rail section, includes:

a clamping structure to be mounted on the rail section for positioning on the rail section for a complete inspection of the weld the following: a transverse top flat phased array transducer, a longitudinal top wedged phased array transducer, and two sets of three longitudinal toe wedged phased array transducers;

the transverse top flat phased array transducer positioned on a head portion of the rail section to provide scanning of the head portion by angular steering of a focused beam;

the longitudinal top wedged phased array transducer positioned on the head portion of the rail section and aligned with a longitudinal symmetry plan of the rail section to provide scanning of a web portion of the rail section; and     the two sets of three longitudinal toe wedged phased array transducers arranged in a side-by-side position and disposed on each side of a toe portion or the rail section, providing scanning of the toe portion of the weld.

The transverse top flat phased array transducer, the longitudinal top wedged phased array transducer, and the two sets of three longitudinal toe wedged phased array transducers may be connected to an electronic beamforming imaging system to provide B-mode scanning images of the weld.

In one implementation, the transverse top flat phased array transducer, the longitudinal top wedged phased array transducer, and the two sets of three longitudinal toe wedged phased array transducers are connected to a multiplexer or switch-box which can select one probe to be activated for inspection at the time.

In another implementation, the electronic beamforming imaging system is provided with flaw level detection software that can determine a threshold of flaw.

According to a third aspect of the invention, a weld inspection ultrasonic device for non-destructive testing of an aluminothermit weld of a rail section, includes:

a clamping structure to be mounted on the rail section for positioning on the rail for a complete inspection of the weld the following: a transverse top flat phased array transducer, a longitudinal top wedged phased array transducer, and a 1.5D or 2D array transducer;

the transverse top flat phased array transducer positioned on a head portion of the rail section to provide scanning of the head portion by angular steering of a focused beam;

the longitudinal top wedged phased array transducer positioned on the head portion of the rail section and aligned with a longitudinal symmetry plan of the rail section to provide scanning of a web portion of the rail section;

the 1.5D or 2D array transducer disposed on a toe portion or the rail section, providing scanning of the toe portion of the weld; and     an electronic beamforming imaging system to provide B-mode scanning images of the weld and to provide beam steering of the 1.5D or 2D array transducer in two perpendicular directions in order to cover the entire volume of the toe portion.

BRIEF DESCRIPTION OF THE SEVERAL VIEWS OF THE DRAWINGS

FIG. 15b a side view of the weld inspection ultrasonic device and the rail section of FIG. 15a.

FIG. 15c is a perspective view of the weld inspection ultrasonic device and the rail section of FIG. 15a.

DETAILED DESCRIPTION OF EXEMPLARY EMBODIMENTS OF THE INVENTION

Flaws and defects that occur in aluminothermit welds are potentially distributed anywhere in the weld section and require a comprehensive method and device to access to all regions of the weld at equal detection relevance and accuracy. The use of phased array ultrasonic transducers is therefore required since the ultrasonic beams must be steered and focused on the interrogative areas. Different types of waves can also be transmitted to the weld to optimize echoes from flaws. Such waves will be delivered using a wedged phased array transducer which is provided with a predetermined angle formed with the rail interface. Furthermore, some regions of the weld can be better inspected using a 1.5 or 2 dimensional array transducer to access to the full volume of the region of interest.

Thermit welds are formed between rails by end-to-end welding. However, the welds often contain flaws, such as bubbles, that must be detected, qualified, and a degree of weakening determined. Therefore, the frequency of the transducers should be optimised to balance between penetration and resolution of the images obtained. For rail inspection, a typical frequency range is between 3.5 MHz and 7 MHz. The exemplary embodiment described herein, uses a 5 MHz, but this value can, of course, be adjusted as needed.

As used herein, the term "rail section" is used to refer to end-to-end welded rails including the weld to be inspected by the present invention. The meaning of the terms "rails," "rail sections," and "welds" in different instances will be readily apparent from the context of the usage of the terms.

Figure 1:
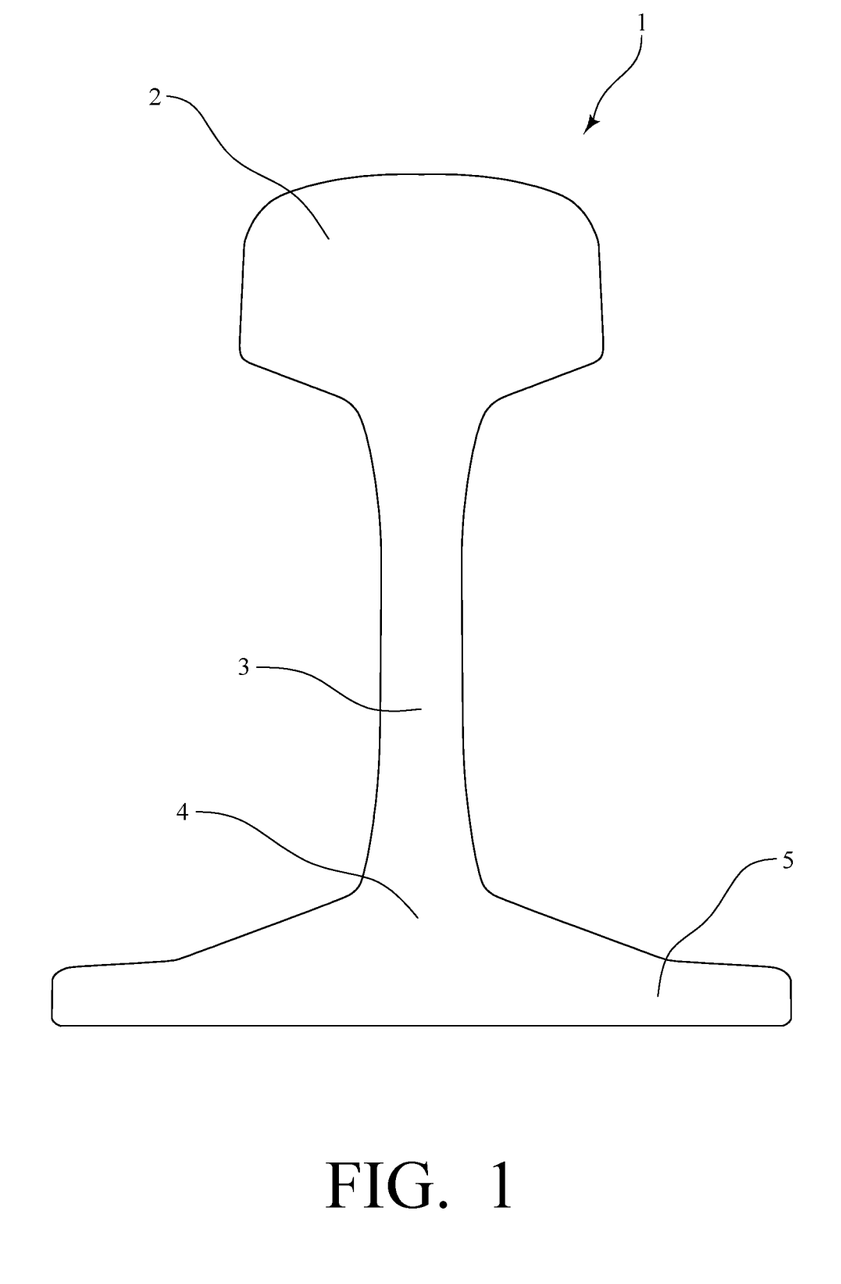
FIG. 1 is a side profile view of a weld of a rail section to be inspected.

FIG. 1 is a side profile view of a rail section 1 showing relative dimensions thereof. The rail section 1 includes four portions, from top to bottom: a head portion 2, a web portion 3, an ankle portion 4, and a toe portion 5. These different portions are characterised by their impact on the weakening of the weld and must be treated with equal attention during inspection. The cross-sections of these portions vary in shape and must be inspected with suitable method and probes. In order to maximize access of an ultrasonic beam to the portions where inspection is desired, the transducer must be placed at certain position on the rail.

FIGS. 2a, 2b, 3a, 3b, 4a, and 4b show different transducer placements to access the portions to be inspected.

Figures 2A, 2B:
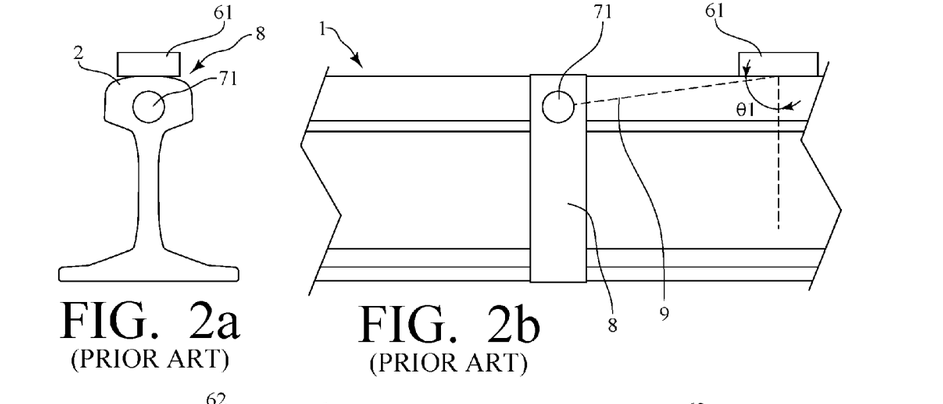
FIGS. 2a, 3a, and 4a are side schematic profile views of rail sections showing the prior art in welded rail inspection using ultrasonic techniques at various inclining angle to provide access to regions of interest in the weld sections.
FIGS. 2b, 3b, and 4b are front schematic profile views of the rail sections of FIGS. 2a, 3a, and 4a, respectively.

In FIGS. 2a and 2b, the rail section 1 is shown with a weld 8 having flaw 71 (represented schematically as a circle) located at the head portion 2. A transducer 61 is positioned on a top surface of the rail section 1 and at a certain distance from the weld 8 in manner such that an acoustic beam 9 forms an angle $\theta 1$ with the vertical so as to direct ultrasonic energy to the desired portion.

Figures 3A, 3B:
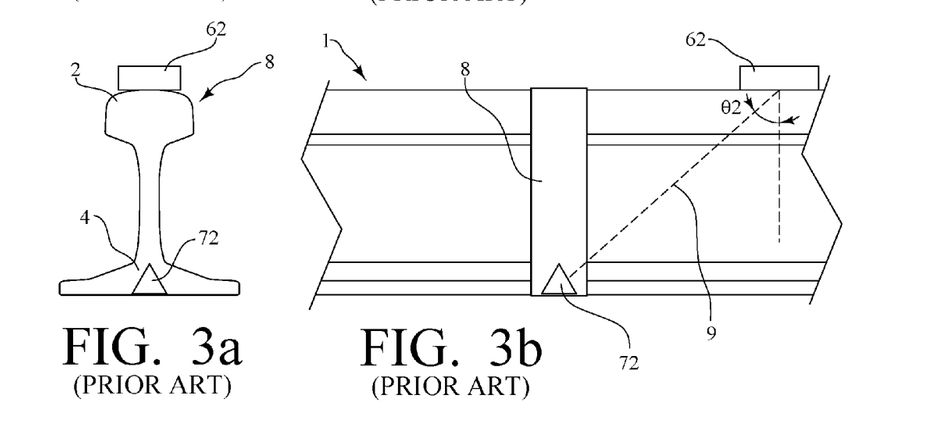

FIGS. 3a and 3b are similar to FIGS. 2a and 2b, wherein a transducer 62 is positioned on the top of the rail section 1 and the acoustic beam 9 forms an angle $\theta 2$ with the vertical so as to direct ultrasonic energy to detect a flaw 72 (represented schematically as a triangle) in the ankle portion 4 of the weld 8.

Figures 4A, 4B:
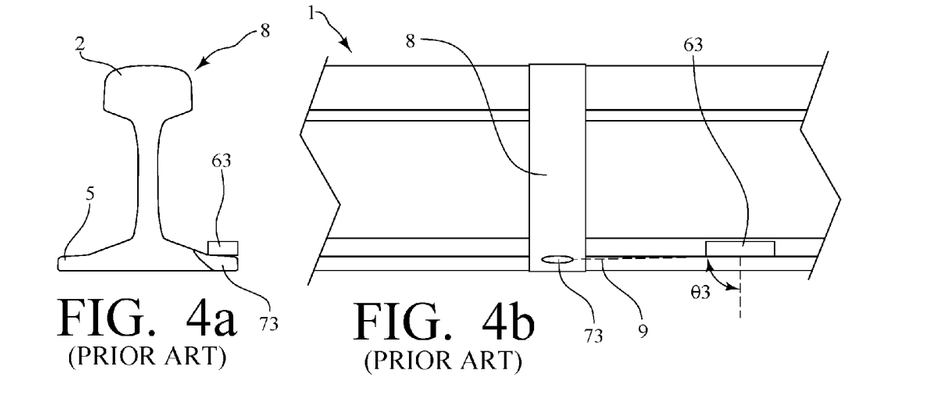

In FIGS. 4a and 4b, a transducer 63 is located on the toe portion 5 of the rail section 1 and its acoustic beam 9 forms an angle $\theta 3$ with the vertical in manner to direct ultrasonic energy to detect a flaw 73 in the toe portion 5 of the weld 8.

More specifically, and according to an exemplary embodiment of the present invention, each portion of the rail section 1 will be inspected with a suitable method that provides optimised acoustic response from the weld structure.

Figure 5:
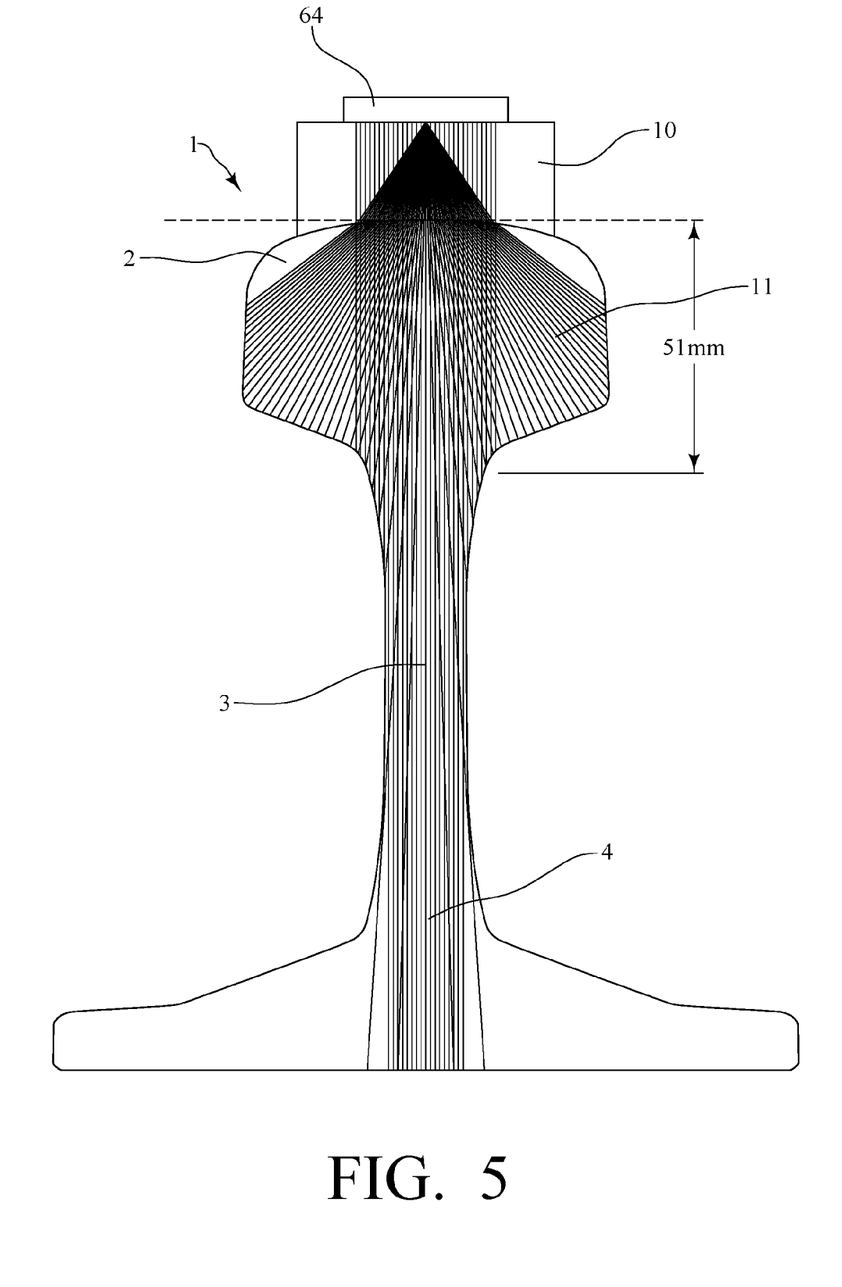
FIG. 5 is a side schematic sectional view of an assembly for scanning portions of a weld.

FIG. 5 shows an assembly for scanning the head portion 2 of a weld with maximum coverage of the volume of the head portion 2. A first transducer 64 of phased array shape is attached to a coupling block 10 to transmit ultrasonic energy to the head portion 2. Coupling between the transducer 64 and the coupling block 10 is obtained with aqueous gel or oil. The transducer 64 is preferably fixed to the block 10 by means of mechanical attachments or screws. The block 10 is provided with an external surface that is conformal to the top surface of the rail section 1 and the corresponding weld. Materials that can be used for the block 10 may be of the group of Lexan, PVC, or the like. The first transducer 64 steers the acoustic focusing beam in a sector shape 11 so that the ultrasonic energy will access a major region of the head portion 2, as illustrated. Moreover, when the beam is approximately at a vertical steering angle the acoustic energy will be propagated through the web portion 3 and the ankle portion 4 so that inspection of these portions is accomplished within the same process. It will be obvious to one skilled in the art that spatial detection resolution in the web and more particularly in the ankle cannot be optimized as performed in the head portion of the weld since the distance from the transducer is much higher.

Figure 6:
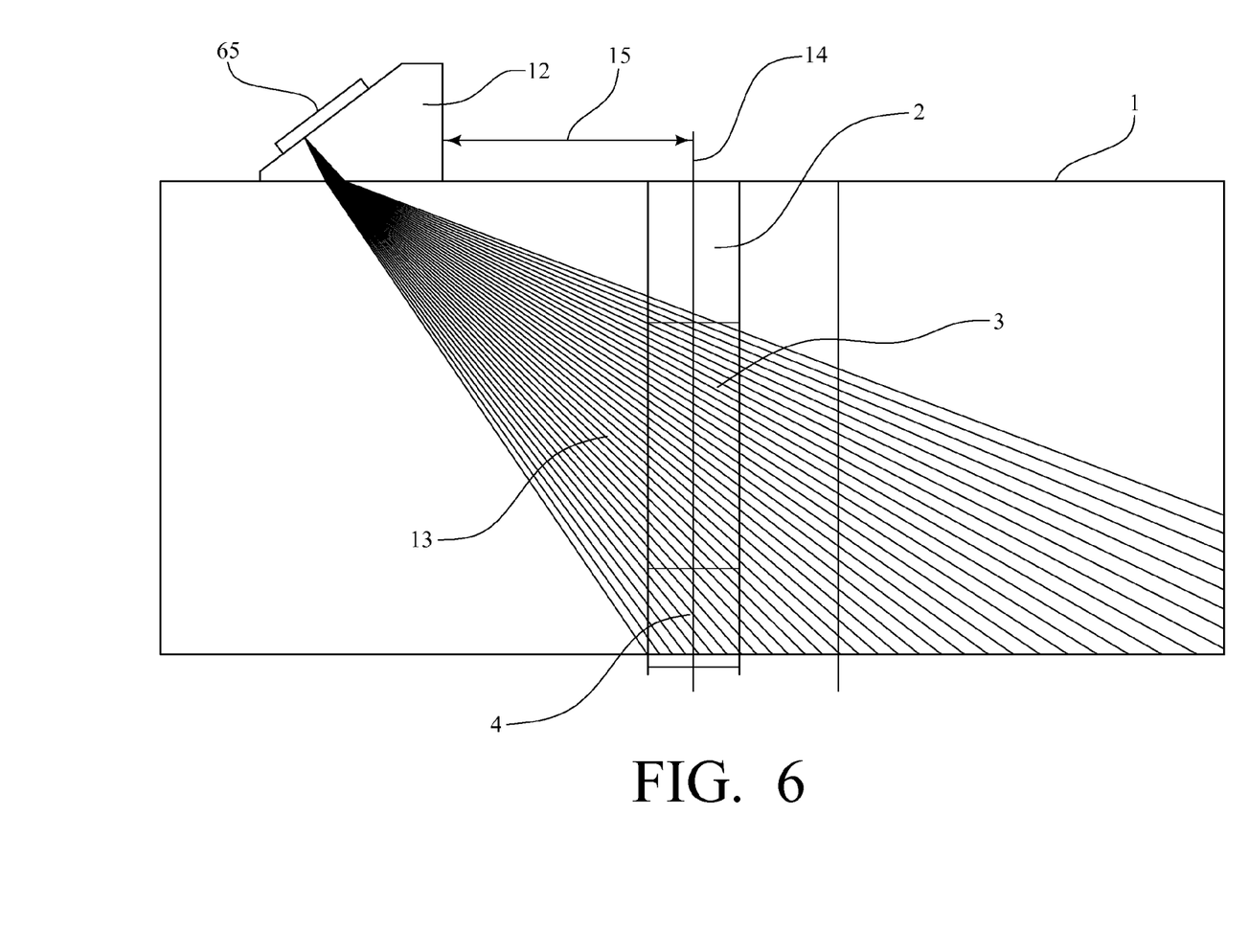
FIG. 6 is a front schematic sectional view of an assembly for scanning portions of a weld.

However, as shown in FIG. 6, a second transducer 65 is attached to a wedge 12 to form an angle with the top surface of the rail section 1. The second transducer 65 and the wedge 12 are placed at a distance 15 from a weld vertical axis 14 so as to spread ultrasonic energy in both the web portion 3 and the ankle portion 4. An ultrasonic energy coverage surface 13 is obtained by electronically steering the acoustic beam of the transducer 65 in predefined angles, and the coverage surface 13 is governed by the difference of the speed of sound at the interface (wedge/rail). Optimization of the distance 15, speed of sound in the wedge 12 and the angle of transducer 65 will allow ultrasonic inspection of web portion 3 and the ankle portion 4 entirely.

Echo data from the first transducer 64 (FIG. 5) and the second transducer 65 (FIG. 6) is combined to enhance detectability and determination of flaws within these portions. This combination can be done by storage of the digital echo data from both transducers, and processing of the data to eliminate artifacts of flaws.

The toe portion 5 must be treated independently since this portion is geometrically differentiated from the rest of the rail section 1. Indeed, this portion cannot be accessed by the first transducer 64 and the second transducer 65. The first transducer 64 is limited by the narrow width of web, while the second transducer 65 is located in the longitudinal plan where toe portion 5 is out of reach.

Figure 7:
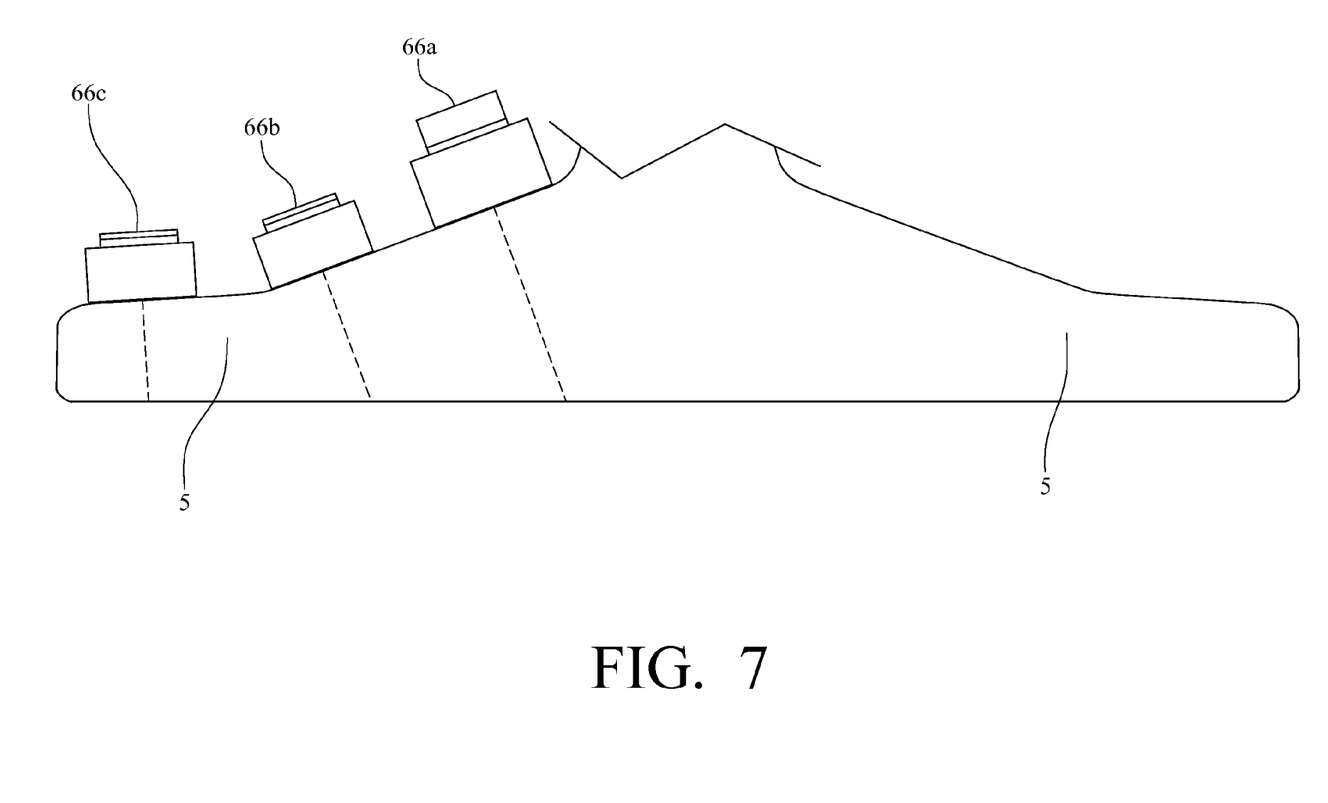
FIG. 7 is a partial side schematic sectional view of an assembly for scanning a toe portion of a weld.

FIG. 7 shows an assembly for inspection of the toe portion 5. It is also noted that the toe portion 5 has two opposite identical portions symmetrically disposed. For the sake of simplicity only one side of the toe portion 5 is currently described. It will be understood that the concept is disclosed for the complete toe portion 5 by adding the symmetrical assembly elements thereto. A third 1.5D or 2D array transducer 66a, a fourth 1.5D or 2D array transducer 66b, and a fifth 1.5D or 2D array transducer 66c are placed on the toe portion 5 at different positions in order to cover the surface of the toe portion 5. The third 1.5D or 2D array transducer 66a, the fourth 1.5D or 2D array transducer 66b, and the fifth 1.5D or 2D array transducer 66c are of phased array type and are attached to respective wedges that provide an angle with the surface of the toe portion 5. The third 1.5D or 2D array transducer 66a, the fourth 1.5D or 2D array transducer 66b, and the fifth 1.5D or 2D array transducer 66c are placed at a horizontal distance from the weld (not visible in the illustration) so as to enable a sufficient steering angle to cover a maximum amount of the toe portion 5. The third 1.5D or 2D array transducer 66a is disposed in immediate proximity to the web portion 3 to examine an area of the toe portion 5 with a highest thickness. The fourth 1.5D or 2D array transducer 66b is placed on a middle area of the toe portion 5 where the thickness is reduced as compared to the area with the highest thickness. The fifth 1.5D or 2D array transducer 66c is located at a peripheral area of the toe portion 5. The third 1.5D or 2D array transducer 66a, the fourth 1.5D or 2D array transducer 66b, and the fifth 1.5D or 2D array transducer 66c are oriented with their elements arranged in longitudinal mode and aligned with the long axis of the rail section 1, as discussed in more detail below.

Figure 8:
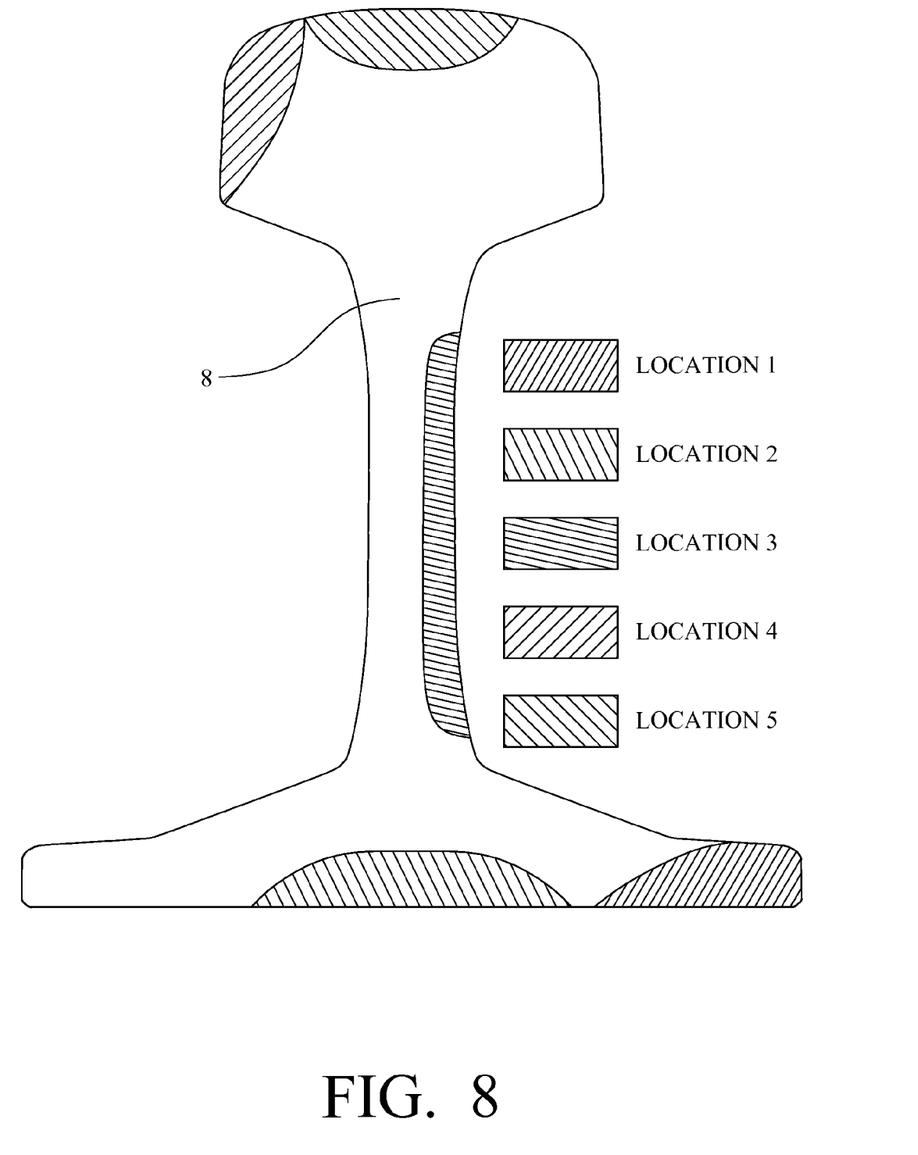
FIG. 8 is a side schematic sectional view of a weld indicating different regions having a high probability of an occurrence of a flaw.

FIG. 8 shows a section of the weld 8 indicating different regions having a high probability of an occurrence of a flaw.

Figure 9A:
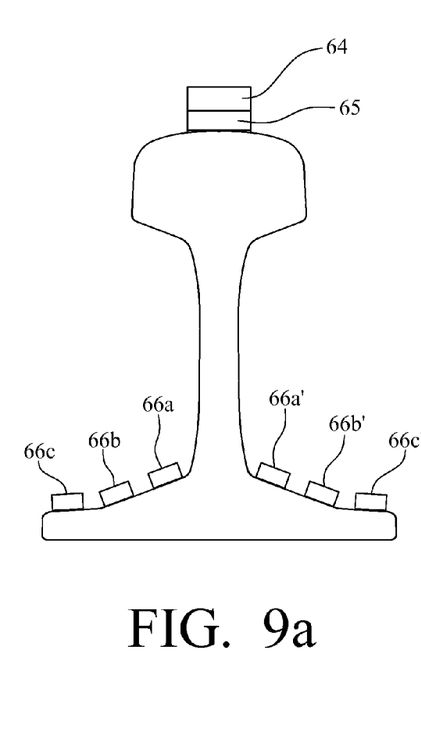
FIG. 9a is a side schematic profile view of an assembly for scanning a weld.
Figure 9B:
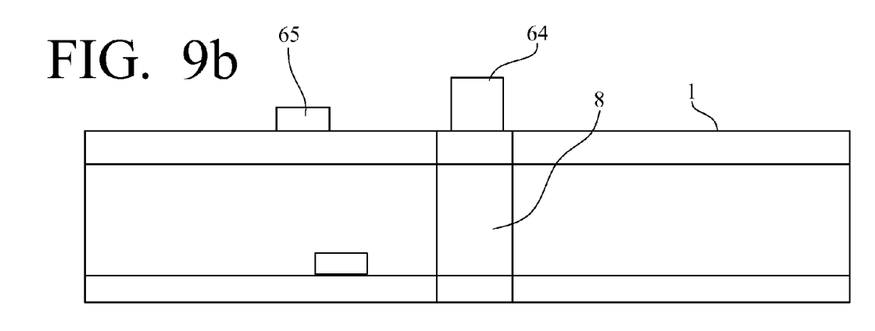
FIG. 9b is a front schematic profile view of an assembly for scanning a weld.
Figure 9C:
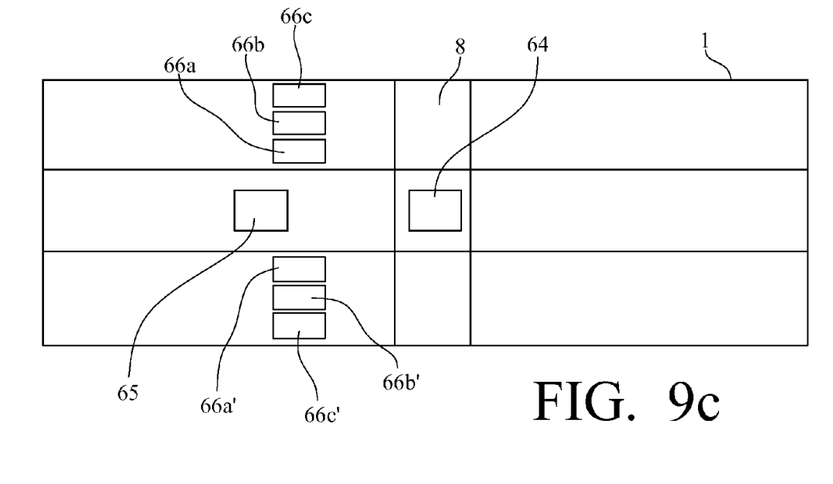
FIG. 9c is a top schematic profile view of an assembly for scanning a weld.

FIGS. 9a, 9b, and 9c summarize the preferred positions of the first transducer 64, the second transducer 65, the third 1.5D or 2D array transducers 66a, 66a', the fourth 1.5D or 2D array transducers 66b, 66b', and the fifth 1.5D or 2D array transducers 66c, 66c' on the rail section 1. It will be noted that only the first transducer 64 is disposed directly on the weld 8, or at the vertical of the weld 8. The other transducers are located at a distance from the weld 8 to provide angular beam steering in the weld 8 or mode conversion for ultrasonic waves. As shown in FIGS. 6 and 7, the second transducer 65, the third 1.5D or 2D array transducers 66a, 66a', the fourth 1.5D or 2D array transducers 66b, 66b', and the fifth 1.5D or 2D array transducers 66c, 66c' are used to transmit longitudinal waves to the portions of the weld 8 at certain obliquity with the wedge-rail interface, and they can also be used to generate Rayleigh waves near to the surface of the rail when using high obliquity angle at the interface. In some circumstances, wedged transducers as described in relation to the assemblies of FIGS. 6 and 7 can generate both longitudinal and Rayleigh waves into the structure by selecting a proper angle of wedge.

Figure 10:
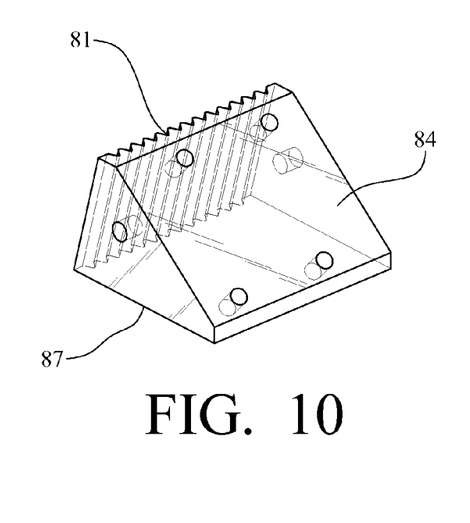
FIG. 10 is a perspective view of an angular wedge to provide an oblique angle to a transducer.
Figure 11:
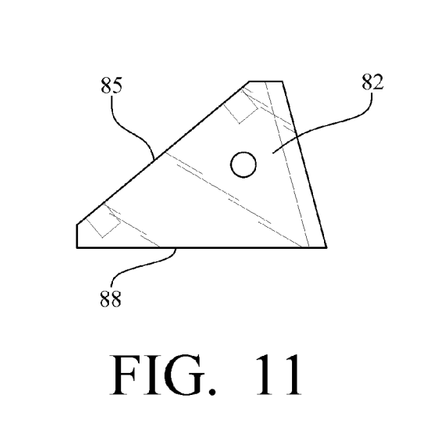
FIG. 11 is a perspective view of another angular wedge to provide an oblique angle to a transducer.
Figure 12:
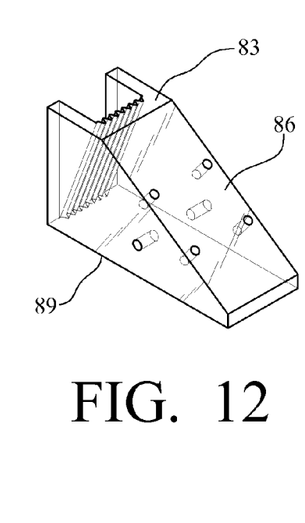
FIG. 12 is a perspective view of another angular wedge to provide an oblique angle to a transducer.
Figure 13:
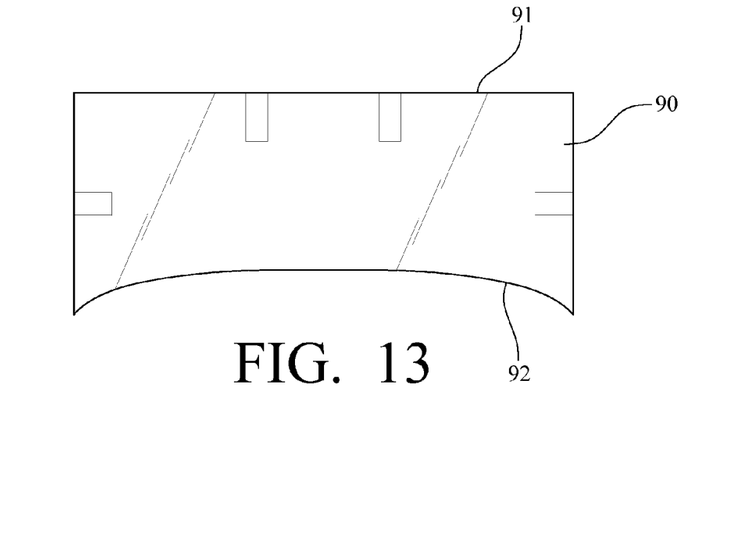
FIG. 13 is a perspective view of coupling block to match a first transducer to a rail head top surface.

As previously described, wedges are needed to provide an oblique angle to the transducers. Some examples of wedges are presented in FIGS. 10-13. FIG. 10, FIG. 11, and FIG. 12 show angular wedges 81, 82, 83 having an oblique surface 84, 85, 86 for attaching a transducer surface, and a bottom flat surface 87, 88, 89 to be coupled to the rail section 1. FIG. 13 shows a coupling block 90 as used in the assembly of FIG. 5 to match the first transducer 64 to the rail head top surface. The coupling block 90 includes a superior flat horizontal surface 91 to host the transducer front face and a curved surface 92 located at the bottom side to conform to the rail head top surface. This curved surface 92 exhibits a radius of curvature according to the type of rail head top surface to which it is to conform.

Figure 14:
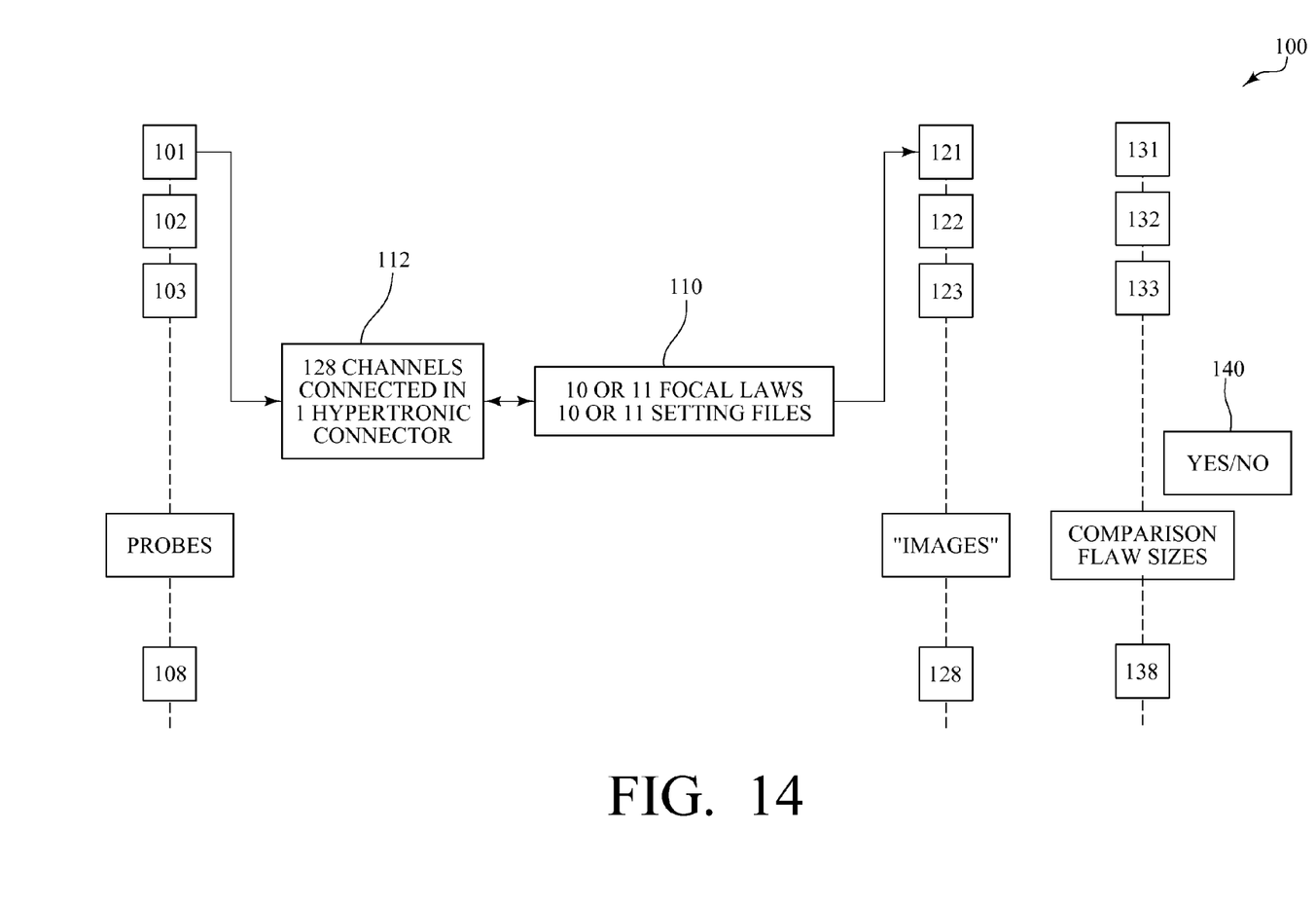
FIG. 14 is a block diagram of an inspection ultrasonic system according to the invention.

FIG. 14 is a block diagram of an inspection ultrasonic system 100 as described herein. Transducers or probes (e.g., 101 to 108) are connected to an electronic beam forming and multiplexing system 110 through a connector 112. The number of channel is selected to be 128 as an example, and will depend on the capability of the electronic beam forming and multiplexing system 110. Different focal laws can be applied to the transducers 101 to 108 to form an image within the structure to be inspected. Images (e.g., 121 to 128) from every transducer (e.g., 101 to 108) will be stored, and signals (e.g., 131 to 138) corresponding to flaws are extracted from the data to be compared and sized. Finally results (e.g., 140) are identified as YES or NO according to predetermined criteria pre-programmed by users.

Figure 15A:
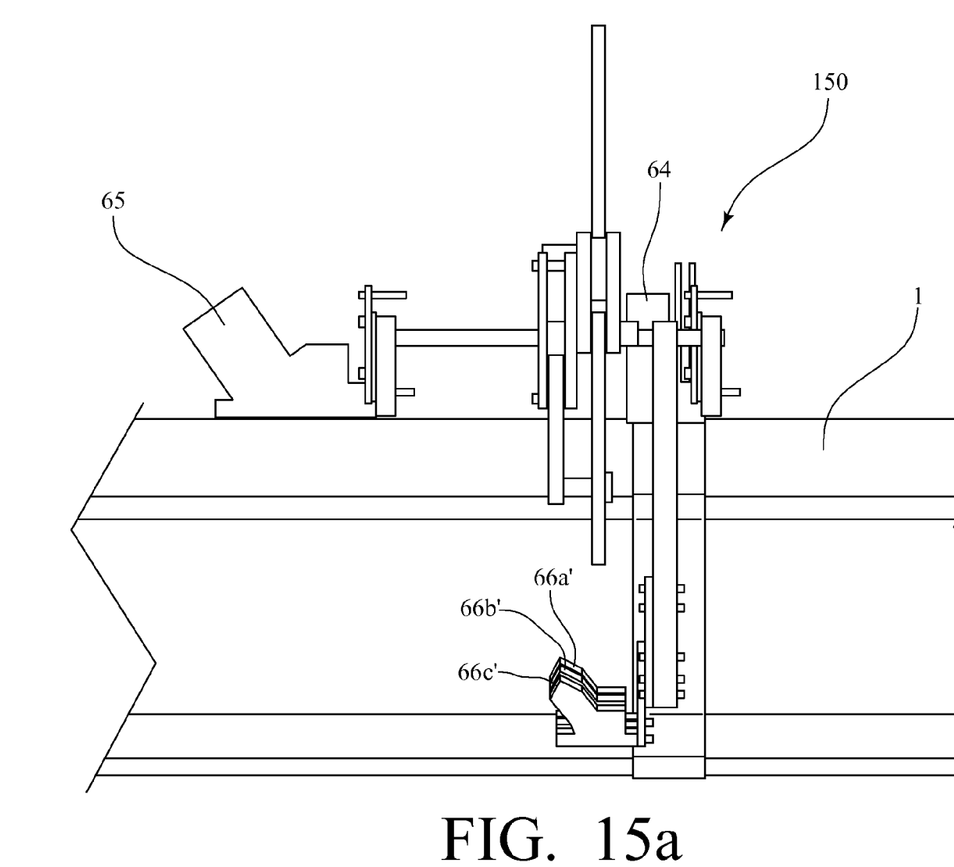
FIG. 15a is a front view of a weld inspection ultrasonic device positioned on a rail section according to the invention.
Figure 15B:
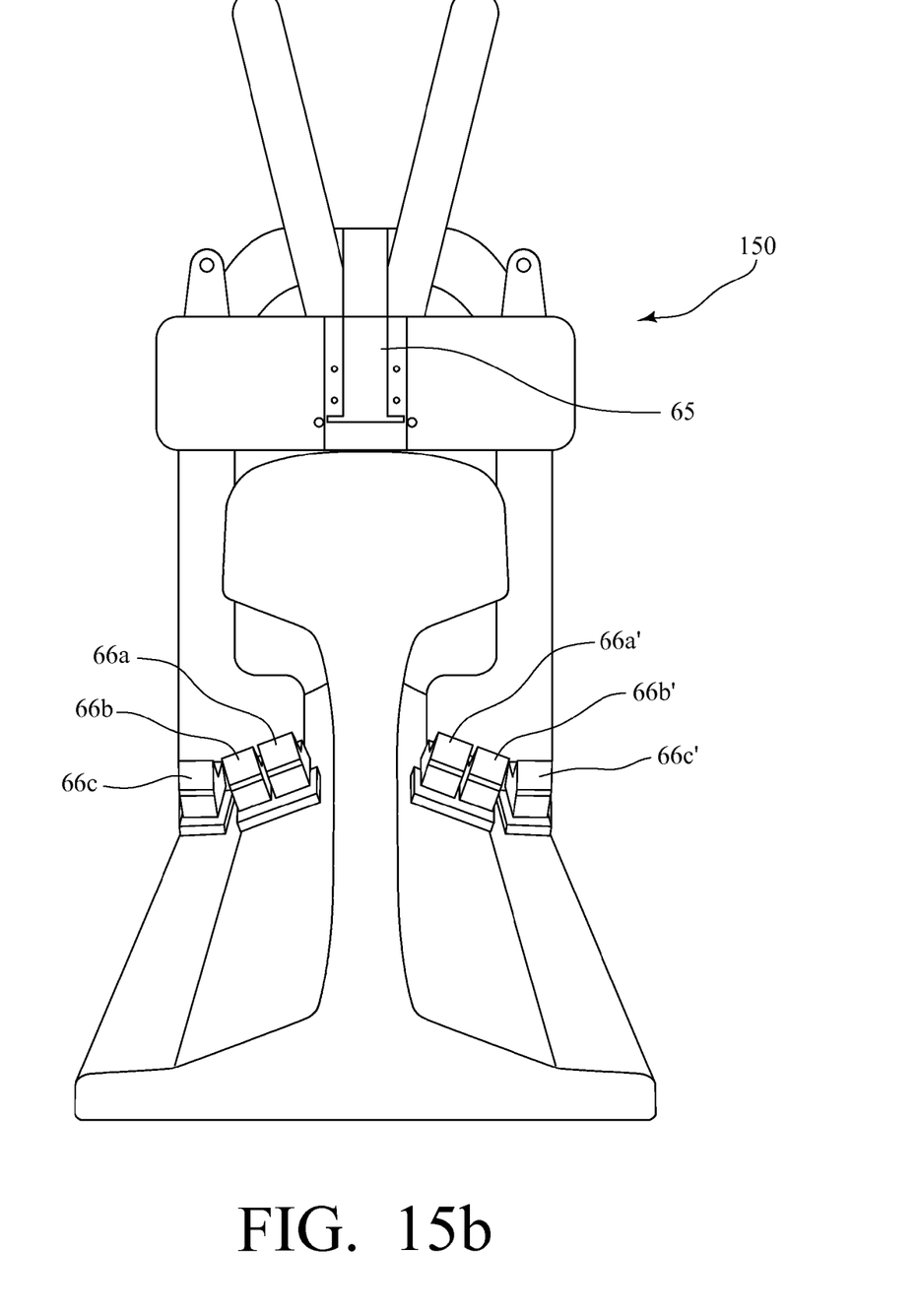
Figure 15C:
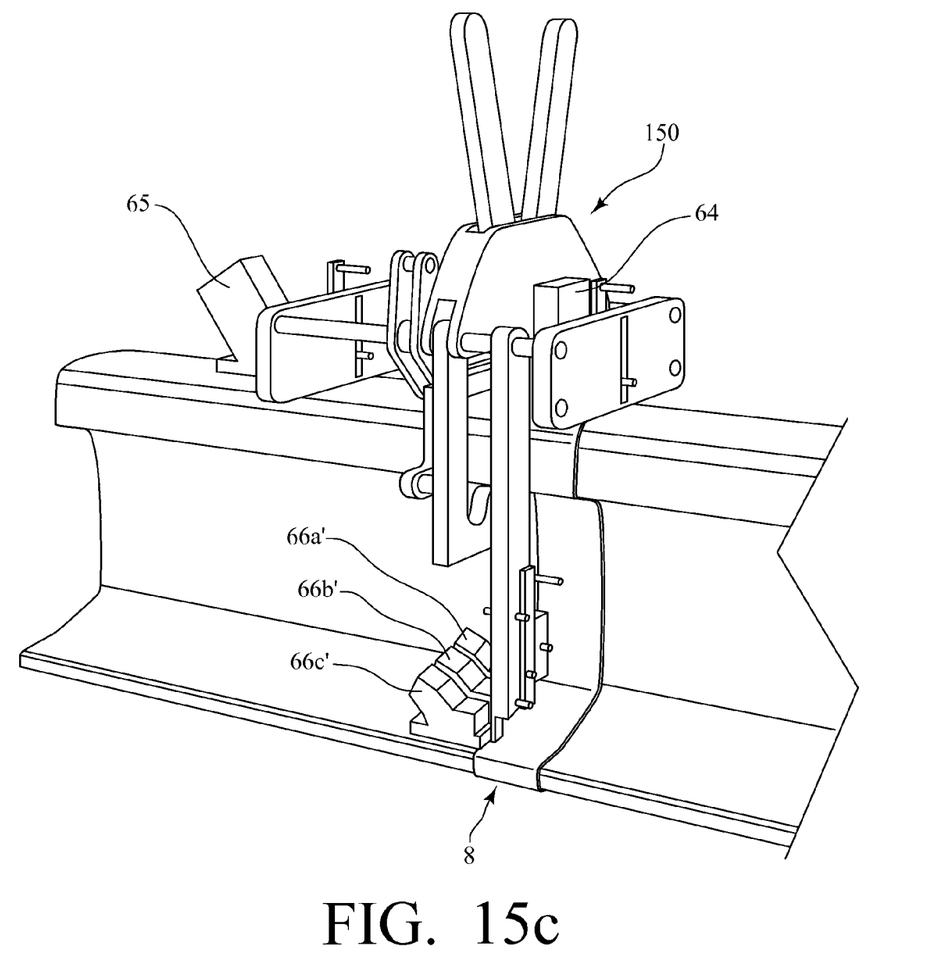

FIGS. 15a, 15b, and 15c, are perspective views of a mechanical clamping device 150 including the first transducer 64, the second transducer 65, the third transducers 66a, 66a', the fourth transducers 66b, 66b', and the fifth transducers 66c, 66c' clamped to a rail section 1. The mechanical clamping device 150 is independently adjustable to modify the distances between the second transducer 65, the third transducers 66a, 66a', the fourth transducers 66b, 66b', and the fifth transducers 66c, 66c' and the weld 8 to optimise flaw detection and coverage.

One of ordinary skill in the art will recognize that additional steps and configurations are possible without departing from the teachings of the invention. This detailed description, and particularly the specific details of the exemplary embodiment disclosed, is given primarily for clearness of understanding and no unnecessary limitations are to be understood therefrom, for modifications will become evident to those skilled in the art upon reading this disclosure and may be made without departing from the spirit or scope of the claimed invention.

What is claimed is:

1. An ultrasonic non-destructive testing method for rail applications using a plurality of phased array transducers to inspect aluminothermit weld defects located in a head portion, a web portion, an ankle portion, and a toe portion of a weld of a rail section, comprising:
    scanning the head portion of the weld including: positioning a first phased array transducer and a second phased array transducer on the head portion of the rail section in aligned configuration for the inspection of the head portion and the web portion of the weld, wherein the first phased array transducer is positioned above the weld and the second phased array transducer is positioned a distance from the first phased array transducer to provide inclined access to the weld; and
    scanning the toe portion of the weld including: positioning a pair of third phased array transducers, a pair of fourth phased array transducers, and a pair of fifth phased array transducers on a surface of the toe portion, such that the pair of third phased array transducers are disposed symmetrically with one of the pair on each side of the toe portion, the pair of fourth phased array transducers are disposed symmetrically with one of the pair on each side of the toe portion, and the pair of fifth phased array transducers are disposed symmetrically with one of the pair on each side of the toe portion;
    wherein the first phased array transducer, the second phased array transducer, the pair of third phased array transducers, the pair of fourth phased array transducers, and the pair of fifth phased array transducers transmit and receive ultrasonic waves in a range between 3.5 MHz and 7 MHz, allowing for the direct focusing of an ultrasonic beam for detection of defects in a selected area of a rail.

2. A weld inspection ultrasonic device for non-destructive testing of an aluminothermit weld of a rail section, comprising:
    a clamping structure to be mounted on the rail section for positioning on the rail section for a complete inspection of the weld the following: a first phased array transducer, a second phased array transducer attached to a wedge, and two sets of third, fourth, and fifth phased array transducers attached to respective wedges;

the first phased array transducer positioned on a head portion of the rail section to provide scanning of the head portion by angular steering of a focused beam;

the second phased array transducer attached to the wedge positioned on the head portion of the rail section and aligned with a longitudinal symmetry plan of the rail section to provide scanning of a web portion of the rail section; and the two sets of third, fourth, and fifth phased array transducers attached to the respective wedges arranged in a side-by-side position and disposed on each side of a toe portion of the rail section, providing scanning of the toe portion of the weld;

wherein the first phased array transducer, the second phased array transducer, the pair of third phased array transducers, the pair of fourth phased array transducers, and the pair of fifth phased array transducers transmit and receive ultrasonic waves in a range between 3.5 MHz and 7 MHz, allowing for the direct focusing of an ultrasonic beam for detection of defects in a selected area of a rail.

3. The weld inspection ultrasonic device for non-destructive testing of an aluminothermit weld according claim 2 wherein, the first phased array transducer, the second phased array transducer, and the two sets of third, fourth, and fifth phased array transducers are connected to an electronic beamforming imaging system to provide B-mode scanning images of the weld.

4. The weld inspection ultrasonic device for non-destructive testing of an aluminothermit weld according claim 2, wherein the first phased array transducer, the second phased array transducer, and the two sets of third, fourth, and fifth phased array transducers are connected to a multiplexer or switch-box which can select one probe to be activated for inspection at a time.

5. The weld inspection ultrasonic device for non-destructive testing of an aluminothermit weld according claim 3, wherein the electronic beamforming imaging system is provided with flaw level detection software that can determine a threshold of flaw.

6. A weld inspection ultrasonic device for non-destructive testing of an aluminothermit weld of a rail section, comprising:

a clamping structure to be mounted on the rail section for positioning on the rail section for a complete inspection of the weld the following: a first phased array transducer, a second phased array transducer attached to a wedge, and a 1.5D or 2D array transducer;

the first phased array transducer positioned on a head portion of the rail section to provide scanning of the head portion by angular steering of a focused beam;

the second phased array transducer attached to the wedge positioned on the head portion of the rail section and aligned with a longitudinal symmetry plan of the rail section to provide scanning of a web portion of the rail section;

the 1.5D or 2D array transducer disposed on a toe portion or the rail section, providing scanning of the toe portion of the weld; and an electronic beamforming imaging system to provide B-mode scanning images of the weld and to provide beam steering of the 1.5D or 2D array transducer in two perpendicular directions in order to cover an entire volume of the toe portion, wherein the first phased array transducer, the second phased array transducer, the pair of third phased array transducers, the pair of fourth phased array transducers, and the pair of fifth phased array transducers transmit and receive ultrasonic waves in a range between 3.5 MHz and 7 MHz, allowing for the direct focusing of an ultrasonic beam for detection of defects in a selected area of a rail.

* * * * *